(12) United States Patent
Tago et al.

(10) Patent No.: US 10,338,031 B2
(45) Date of Patent: Jul. 2, 2019

(54) COMPONENT-EMBEDDED SUBSTRATE AND SUBSTRATE FLAW DETECTING METHOD

(71) Applicant: Murata Manufacturing Co., Ltd., Nagaokakyo-shi, Kyoto-fu (JP)

(72) Inventors: Shigeru Tago, Nagaokakyo (JP); Hirofumi Shinagawa, Nagaokakyo (JP); Toshiro Adachi, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 240 days.

(21) Appl. No.: 15/446,092

(22) Filed: Mar. 1, 2017

(65) Prior Publication Data

US 2017/0176392 A1    Jun. 22, 2017

Related U.S. Application Data

(63) Continuation of application No. PCT/JP2015/073952, filed on Aug. 26, 2015.

(30) Foreign Application Priority Data

Sep. 3, 2014  (JP) .................................. 2014-178685

(51) Int. Cl.
*G01N 29/04* (2006.01)
*H01L 23/00* (2006.01)
(Continued)

(52) U.S. Cl.
CPC ........... *G01N 29/043* (2013.01); *G01N 29/11* (2013.01); *H01L 23/00* (2013.01);
(Continued)

(58) Field of Classification Search
CPC ...... G01N 29/043; G01N 29/11; H01L 23/00; H01L 23/5383; H01L 23/5384;
(Continued)

(56) References Cited

U.S. PATENT DOCUMENTS

| 6,740,975 B2 * | 5/2004 | Nakanishi ............ H05K 1/0224 257/691 |
| 2002/0036054 A1 | 3/2002 | Nakatani et al. |

(Continued)

FOREIGN PATENT DOCUMENTS

| JP | 4-207099 A | 7/1992 |
| JP | 11-112142 A | 4/1999 |

(Continued)

OTHER PUBLICATIONS

Official Communication issued in International Patent Application No. PCT/JP2015/073952, dated Nov. 10 2015.

*Primary Examiner* — Justin Seo
*Assistant Examiner* — David Z Huang
(74) *Attorney, Agent, or Firm* — Keating & Bennett, LLP (57) ABSTRACT

A component-embedded substrate includes a multilayer body including a plurality of insulating layers stacked in a stacking direction, an embedded component embedded in the multilayer body, and planar conductors disposed on both sides of the embedded component in the stacking direction, the planar conductors overlapping the embedded component. The planar conductors each include a plurality of openings that overlap the embedded component over substantially the entire region occupied by the embedded component, as seen in the stacking direction.

20 Claims, 5 Drawing Sheets

(51) Int. Cl.
*G01N 29/11* (2006.01)
*H01L 23/538* (2006.01)
*H01L 23/552* (2006.01)
*H01L 25/065* (2006.01)
*H05K 1/02* (2006.01)
*H05K 1/18* (2006.01)

(52) U.S. Cl.
CPC ...... *H01L 23/5383* (2013.01); *H01L 23/5384* (2013.01); *H01L 23/552* (2013.01); *H01L 24/16* (2013.01); *H01L 25/0657* (2013.01); *H05K 1/0218* (2013.01); *H05K 1/0269* (2013.01); *G01N 2291/015* (2013.01); *G01N 2291/048* (2013.01); *G01N 2291/2697* (2013.01); *H01L 23/5386* (2013.01); *H01L 23/5389* (2013.01); *H01L 2224/04105* (2013.01); *H01L 2224/16227* (2013.01); *H01L 2225/06517* (2013.01); *H01L 2225/06548* (2013.01); *H01L 2225/06555* (2013.01); *H01L 2924/14* (2013.01); *H01L 2924/3025* (2013.01); *H01L 2924/3512* (2013.01); *H05K 1/185* (2013.01); *H05K 2203/0285* (2013.01)

(58) Field of Classification Search
CPC ... H01L 23/552; H01L 24/16; H01L 25/0657; H05K 1/0218; H05K 1/0269
See application file for complete search history.

(56) References Cited

U.S. PATENT DOCUMENTS

| | | |
|---|---|---|
| 2002/0153611 A1 | 10/2002 | Nakanishi |
| 2004/0160752 A1 | 8/2004 | Yamashita et al. |
| 2017/0115254 A1* | 4/2017 | Ratering .............. G01N 29/226 |

FOREIGN PATENT DOCUMENTS

| | | |
|---|---|---|
| JP | 2002-324979 A | 11/2002 |
| JP | 2004-134669 A | 4/2004 |
| JP | 2004-274035 A | 9/2004 |
| JP | 2008-153693 A | 7/2008 |
| JP | 2012-195468 A | 10/2012 |
| JP | 2014-107515 A | 6/2014 |

* cited by examiner

COMPONENT-EMBEDDED SUBSTRATE AND SUBSTRATE FLAW DETECTING METHOD

This application claims the benefit of priority to Japanese Patent Application No. 2014-178685 filed on Sep. 3, 2014 and is a Continuation Application of PCT Application No. PCT/JP2015/073952 filed on Aug. 26, 2015. The entire contents of each application are hereby incorporated herein by reference.

BACKGROUND OF THE INVENTION

1. Field of the Invention

The present invention relates to a technique for non-destructively inspecting an internal structure of a component-embedded substrate including an embedded component therein. In particular, the present invention relates to a component-embedded substrate having a configuration suitable for non-destructively detecting cracks in the substrate, and also relates to a substrate flaw detecting method.

2. Description of the Related Art

A substrate flaw detecting method has been often applied to a component-embedded substrate for checking for cracks in and around an embedded component.

In a component-embedded substrate of the related art, an embedded component, such as an integrated circuit (IC) chip, is often electromagnetically shielded to eliminate electromagnetic noise originating from the embedded component, or to prevent the embedded component from being affected by electromagnetic noise from the outside (see, e.g., Japanese Unexamined Patent Application Publication No. 2004-134669). In the component-embedded substrate disclosed in Japanese Unexamined Patent Application Publication No. 2004-134669, the embedded IC chip is electromagnetically shielded by a metal film covering the embedded IC chip.

In the component-embedded substrate disclosed in Japanese Unexamined Patent Application Publication No. 2004-134669, since the embedded IC chip is electromagnetically shielded on the top side thereof by the metal film, a non-destructive inspection performed from the top side of the embedded IC chip to check for cracks using ultrasonic waves, X-rays, or infrared rays may be blocked by a shield electrode.

SUMMARY OF THE INVENTION

Accordingly, preferred embodiments of the present invention provide component-embedded substrates including an internal structure that is able to be non-destructively inspected with high accuracy from a side of a planar conductor covering an embedded component, and also provide substrate flaw detecting methods.

A component-embedded substrate according to a preferred embodiment of the present invention includes a multilayer body including a plurality of insulating layers stacked in a stacking direction; an embedded component embedded in the multilayer body; a planar conductor disposed on one side of the embedded component in the stacking direction, the planar conductor overlapping the embedded component; and one or more conductors disposed on the one side of the embedded component in the stacking direction, the one or more conductors being different from the planar conductor. The planar conductor includes a plurality of overlapping the embedded component over substantially the entire region occupied by the embedded component, as seen in the stacking direction. At least some of the plurality of openings do not overlap any of the one or more conductors different from the planar conductor, as seen in the stacking direction.

In this configuration, the planar conductor overlapping the embedded component includes a plurality of openings. This allows flaw detection waves, such as ultrasonic waves, X-rays, or infrared rays, transmitted from one side in the stacking direction to pass through the openings in the planar conductor and easily reach the embedded component and its vicinity. It is thus possible to non-destructively inspect the internal structure of the component-embedded substrate with high accuracy.

Also, with this configuration, flaw detection waves transmitted to the embedded component and its vicinity are able to be prevented from being blocked by the one or more conductors.

The one or more conductors preferably include a line conductor extending around the openings while overlapping the embedded component and the planar conductor, as seen in the stacking direction. With this configuration, transmission of ultrasonic waves to the embedded component and its vicinity is able to be prevented from being blocked by the line conductor.

The planar conductor is preferably connected to a ground potential. This configuration is preferable particularly when the embedded component includes an active element. In this case, the embedded component is able to be electromagnetically shielded by the planar conductor. Even when the embedded component is an active element that originates noise, the planar conductor is able to prevent electromagnetic noise from leaking out.

It is preferable that the plurality of openings in the planar conductor be regularly arranged. For example, the planar conductor may have a mesh shape or a lattice shape, as seen through the multilayer body in the stacking direction. Thus, since ultrasonic waves are able to be transmitted to the embedded component and a wide area therearound through the openings dispersedly arranged, it is possible to check for cracks with uniform accuracy.

It is preferable that a plurality of planar conductors be provided, and that the plurality of planar conductors be disposed on both the one side and the other side of the embedded component in the stacking direction. The embedded component is thus electromagnetically shielded on the one and the other sides thereof in the stacking direction.

A substrate flaw detecting method according to another preferred embodiment of the present invention preferably includes transmitting ultrasonic waves from one side of the component-embedded substrate in the stacking direction, receiving the ultrasonic waves transmitted through the component-embedded substrate, and obtaining information of an internal structure of the component-embedded substrate based on an intensity of the ultrasonic waves received.

In preferred embodiments of the present invention described above, even when the planar conductor overlapping the embedded component is provided, ultrasonic waves are able to pass through the plurality of openings in the planar conductor. This makes it possible to check for cracks in and around the embedded component using ultrasonic waves with high accuracy.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Component-embedded substrates according to preferred embodiments of the present invention will now be described.

Figure 1A:
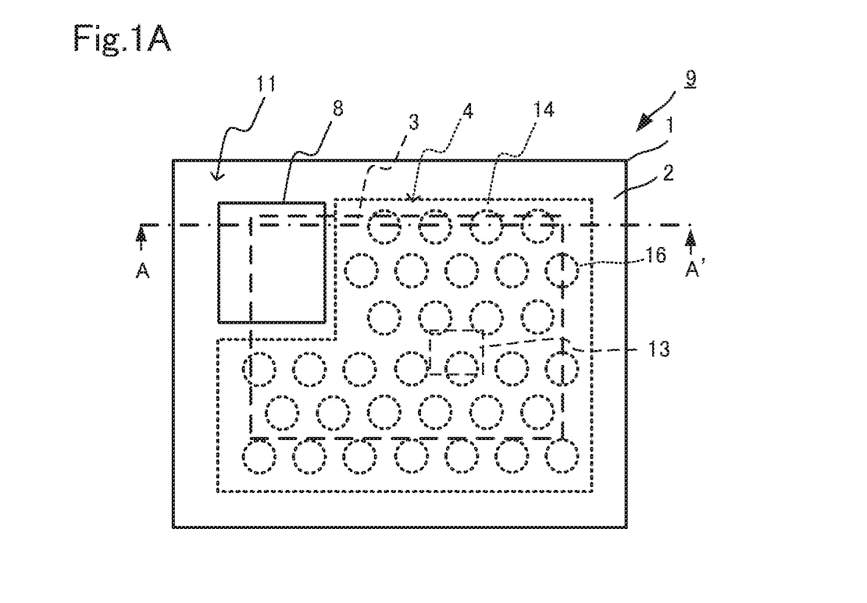
FIGS. 1A and 1B illustrate a main portion of a component-embedded substrate according to a preferred embodiment of the present invention.
Figure 1B:
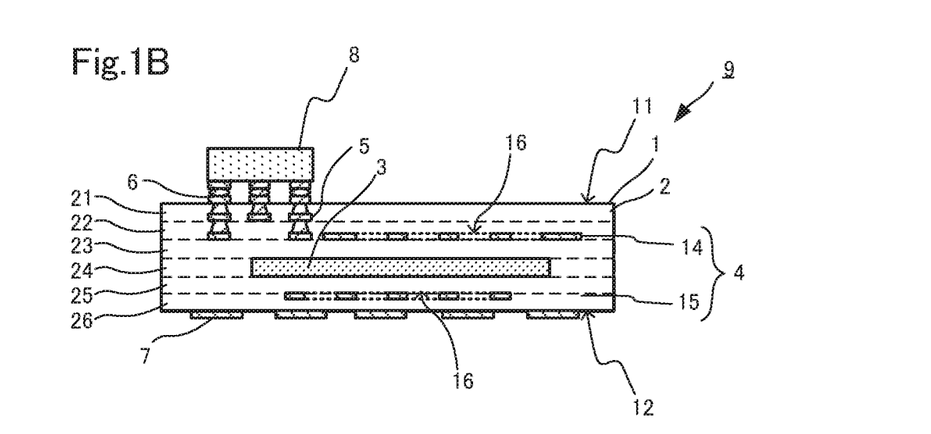

FIG. 1A is a perspective plan view illustrating a main portion of a module component 9 including a component-embedded substrate 1 according to a preferred embodiment of the present invention. FIG. 1B is a lateral cross-sectional view illustrating the main portion of the module component 9 including the component-embedded substrate 1.

The module component 9 includes the component-embedded substrate 1 and a surface mount device 8. The component-embedded substrate 1 is a plate-shaped member which is thin in the thickness direction. The component-embedded substrate 1 includes a top surface 11 and a bottom surface 12 perpendicular or substantially perpendicular to the thickness direction. The surface mount device 8 is surface-mounted on the top surface 11 of the component-embedded substrate 1. The surface mount device 8 is a filter component here.

The component-embedded substrate 1 includes a multilayer body 2, an embedded component 3, a shield electrode 4, a wiring portion 5, a component connecting portion 6, and an external connecting portion 7. The multilayer body 2 is a flat plate which is thin in the thickness direction, and is made of insulating ceramic or insulating resin. The multilayer body 2 is obtained preferably by stacking a total of six insulating layers 21, 22, 23, 24, 25, and 26 in the thickness direction (stacking direction). The embedded component 3 is embedded in the multilayer body 2. The embedded component 3 includes an oscillation circuit 13 including an active element, and its peripheral circuit. The shield electrode 4 is disposed inside the multilayer body 2, and is connected to the ground potential to electromagnetically seal the embedded component 3. The wiring portion 5 is disposed inside the multilayer body 2, and is electrically connected to the surface mount device 8 and the embedded component 3. The component connecting portion 6 is disposed on the top surface 11 of the multilayer body 2, and is electrically and physically connected to the surface mount device 8. The external connecting portion 7 is disposed on the bottom surface 12 of the multilayer body 2, and is electrically and physically connected to an external substrate.

As illustrated in FIG. 1A, the surface mount device 8 is preferably rectangular or substantially rectangular in plan view. The embedded component 3 is also preferably rectangular or substantially rectangular in plan view, as seen through the multilayer body 2. The surface mount device 8 is positioned to partly overlap one of corner portions of the embedded component 3 in plan view. The oscillation circuit 13 is embedded in the embedded component 3 at a position distant from the region where the embedded component 3 and the surface mount device 8 overlap.

The shield electrode 4 includes planar conductors 14 and 15 that overlap the embedded component 3 in plan view of the multilayer body 2. In the multilayer body 2, the planar conductor 14 is disposed on one side of the embedded component 3 adjacent to the top surface 11, whereas the planar conductor 15 is disposed on the other side of the embedded component 3 adjacent to the bottom surface 12. That is, in the multilayer body 2, the planar conductor 14 is disposed on the one side of the embedded component 3 adjacent to the top surface 11 so as to overlap the embedded component 3, as seen through from the top surface 11. Similarly, in the multilayer body 2, the planar conductor 15 is disposed on the other side of the embedded component 3 adjacent to the bottom surface 12 so as to overlap the embedded component 3, as seen through from the bottom surface 12. As seen through from the top surface 11, the planar conductor 14 overlaps substantially the entire region occupied by the embedded component 3, except for the region where the embedded component 3 and the surface mount device 8 partly overlap, such that the planar conductor 14 covers the entire oscillation circuit 13. As seen through from the bottom surface 12, the planar conductor 15 overlaps substantially the entire region occupied by the embedded component 3, including a portion of the region where the embedded component 3 and the surface mount device 8 partly overlap, such that the planar conductor 15 covers the entire oscillation circuit 13.

The planar conductor 14 and the planar conductor 15 each include a plurality of circular openings 16 dispersedly arranged to overlap substantially the entire region occupied by the embedded component 3, as seen from the top surface 11 or bottom surface 12. The openings 16 preferably have a diameter that facilitates transmission of flaw detection waves, such as ultrasonic waves, X-rays, or infrared rays. In this example, the diameter of the openings 16 is preferably about 120 µm, for example, which facilitates transmission of ultrasonic waves. The openings 16 in the planar conductor 14 and the openings 16 in the planar conductor 15 are arranged to face each other.

Figure 2A:
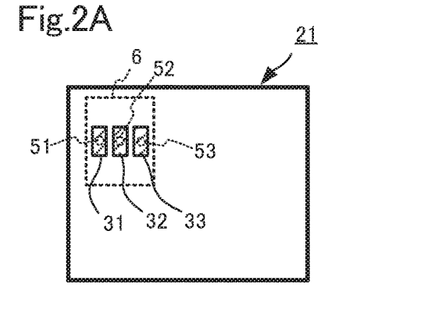
FIGS. 2A-2F are exploded plan views each illustrating an insulating layer included in the component-embedded substrate according to a preferred embodiment of the present invention.

FIG. 2A is a plan view of the insulating layer 21 as seen from the top surface 11. The insulating layer 21 is the first insulating layer from the top surface 11 of the multilayer body 2, that is, an insulating layer exposed to the top surface 11. A surface of the insulating layer 21 on the side of the top surface 11 is provided with the component connecting portion 6. The component connecting portion 6 includes component connecting electrodes 31, 32, and 33.

The component connecting electrodes 31, 32, and 33 are preferably pad conductors, which are arranged in this order in the width direction. The component connecting electrode 32 located in the center is connected to a ground terminal of the surface mount device (filter component) 8. The component connecting electrode 31 located to the left of the component connecting electrode 32 in the width direction is connected to a filter output terminal of the surface mount device (filter component) 8. The component connecting electrode 33 located to the right of the component connecting electrode 32 in the width direction is connected to a filter input terminal of the surface mount device (filter component) 8.

The insulating layer 21 includes interlayer connection conductors 51, 52, and 53 defining the wiring portion 5. The interlayer connection conductor 51 passes through the insulating layer 21, and is connected to the component connecting electrode 31 at an end portion thereof on the side of the top surface 11. The interlayer connection conductor 52 passes through the insulating layer 21, and is connected to the component connecting electrode 32 at an end portion thereof on the side of the top surface 11. The interlayer connection conductor 53 passes through the insulating layer 21, and is connected to the component connecting electrode 33 at an end portion thereof on the side of the top surface 11.

Figure 2B:
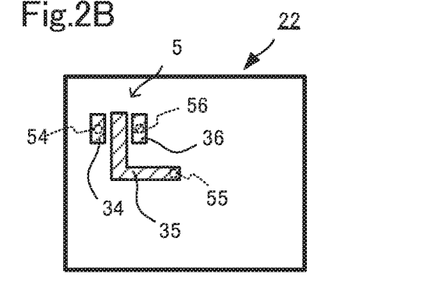

FIG. 2B is a plan view of the insulating layer 22 as seen from the top surface 11. The insulating layer 22 is the second insulating layer from the top surface 11 of the multilayer body 2. A surface of the insulating layer 22 on the side of the top surface 11 is provided with a pad conductor 34, a line conductor 35, and a pad conductor 36 defining the wiring portion 5.

The pad conductor 34 is connected to an end portion of the interlayer connection conductor 51 on the side of the bottom surface 12, and is further connected to the filter output terminal of the surface mount device 8, with the interlayer connection conductor 51 and the component connecting electrode 31 interposed therebetween. The line conductor 35 is connected to an end portion of the interlayer connection conductor 52 on the side of the bottom surface 12, and is further connected to the ground terminal of the surface mount device 8, with the interlayer connection conductor 52 and the component connecting electrode 32 interposed therebetween. On the surface of the insulating layer 22 on the side of the top surface 11, the line conductor 35 extends from a corner portion corresponding to the surface mount device 8 mounted on the top surface 11 to a center portion overlapping the shield electrode 4 (planar conductor 14) described below. Then, in the center portion overlapping the shield electrode 4 (planar conductor 14), the line conductor 35 extends around a region facing the openings 16 so as not to overlap the openings 16 in the stacking direction. The pad conductor 36 is connected to an end portion of the interlayer connection conductor 53 on the side of the bottom surface 12, and is further connected to the filter input terminal of the surface mount device 8, with the interlayer connection conductor 53 and the component connecting electrode 33 interposed therebetween.

As described above, the line conductor 35, which is a conductor different from the planar conductor 14, is shaped and routed such that the line conductor 35 does not cover the openings 16. Therefore, even when the line conductor 35 extends to overlap the planar conductor 14 in the stacking direction, flaw detection waves, such as ultrasonic waves, X-rays, or infrared rays, are able to reach the embedded component 3 and its vicinity through the openings 16 without being blocked by the line conductor 35.

The insulating layer 22 includes interlayer connection conductors 54, 55, and 56 defining the wiring portion 5. The interlayer connection conductor 54 passes through the insulating layer 22, and is connected to the pad conductor 34 at an end portion thereof on the side of the top surface 11. The interlayer connection conductor 55 passes through the insulating layer 22, and is connected to the line conductor 35 at an end portion thereof on the side of the top surface 11. The interlayer connection conductor 56 passes through the insulating layer 22, and is connected to the pad conductor 36 at an end portion thereof on the side of the top surface 11.

Figure 2C:
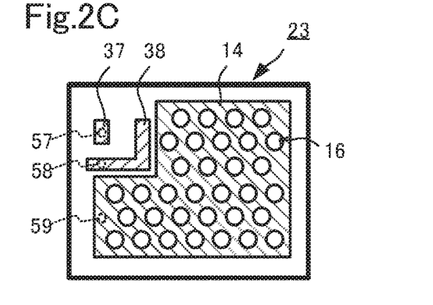

FIG. 2C is a plan view of the insulating layer 23 as seen from the top surface 11. The insulating layer 23 is the third insulating layer from the top surface 11 of the multilayer body 2. A surface of the insulating layer 23 on the side of the top surface 11 is provided with a pad conductor 37 and a line conductor 38 defining the wiring portion 5, and is also provided with the planar conductor 14 forming the shield electrode 4.

The pad conductor 37 is connected to an end portion of the interlayer connection conductor 54 on the side of the bottom surface 12, and is further connected to the filter output terminal of the surface mount device 8, with the interlayer connection conductors 54 and 51, the pad conductor 34, and the component connecting electrode 31 interposed therebetween. The line conductor 38 is connected to an end portion of the interlayer connection conductor 56 on the side of the bottom surface 12, and is further connected to the filter input terminal of the surface mount device 8, with the interlayer connection conductors 56 and 53, the pad conductor 36, and the component connecting electrode 33 interposed therebetween. Then, on the surface of the insulating layer 23 on the side of the top surface 11, the line conductor 38 extends to a predetermined point near the outer edge in a corner portion corresponding to the surface mount device 8 mounted on the top surface 11. The planar conductor 14 defining the shield electrode 4 is connected to an end portion of the interlayer connection conductor 55 on the side of the bottom surface 12, and is further connected to the ground terminal of the surface mount device 8, with the interlayer connection conductors 55 and 52, the line conductor 35, and the component connecting electrode 32 interposed therebetween.

The insulating layer 23 includes interlayer connection conductors 57, 58, and 59 defining the wiring portion 5. The interlayer connection conductor 57 passes through the insulating layer 23, and is connected to the pad conductor 37 at an end portion thereof on the side of the top surface 11. The interlayer connection conductor 58 passes through the insulating layer 23, and is connected to the line conductor 38 at an end portion thereof on the side of the top surface 11. The interlayer connection conductor 59 passes through the insulating layer 23, and is connected to the planar conductor 14 at an end portion thereof on the side of the top surface 11.

Figure 2D:
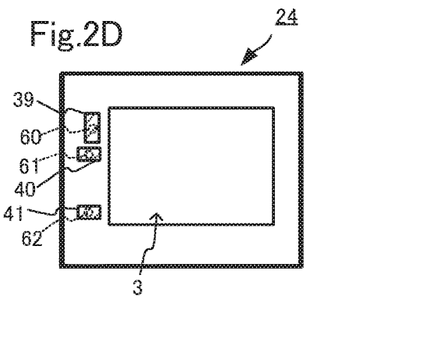

FIG. 2D is a plan view of the insulating layer 24 as seen from the top surface 11. The insulating layer 24 is the fourth insulating layer from the top surface 11 of the multilayer body 2. The insulating layer 24 has a cavity, in which the embedded component 3 is embedded. A surface of the insulating layer 24 surrounding the embedded component 3 on the side of the top surface 11 is provided with pad conductors 39, 40, and 41 defining the wiring portion 5.

The pad conductor 39 is connected to an end portion of the interlayer connection conductor 57 on the side of the bottom surface 12, and is further connected to the filter output terminal of the surface mount device 8, with the interlayer connection conductors 57, 54, and 51, the pad conductors 37 and 34, and the component connecting electrode 31 interposed therebetween. The pad conductor 40 is connected to an end portion of the interlayer connection conductor 58 on the side of the bottom surface 12, and is further connected to the filter input terminal of the surface mount device 8, with the interlayer connection conductors 58, 56, and 53, the line conductor 38, the pad conductor 36, and the component connecting electrode 33 interposed therebetween. The pad conductor 41 is connected to an end portion of the interlayer connection conductor 59 on the side of the bottom surface 12, and is further connected to the ground terminal of the surface mount device 8, with the interlayer connection conductors 59, 55, and 52, the planar conductor 14, the line conductor 35, and the component connecting electrode 32 interposed therebetween.

The insulating layer 24 includes interlayer connection conductors 60, 61, and 62 defining the wiring portion 5. The interlayer connection conductor 60 passes through the insulating layer 24, and is connected to the pad conductor 39 at an end portion thereof on the side of the top surface 11. The interlayer connection conductor 61 passes through the insulating layer 24, and is connected to the pad conductor 40 at an end portion thereof on the side of the top surface 11. The interlayer connection conductor 62 passes through the insulating layer 24, and is connected to the pad conductor 41 at an end portion thereof on the side of the top surface 11.

Figure 2E:
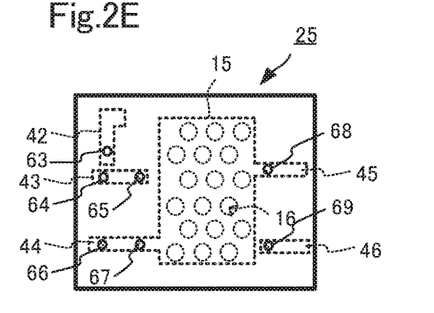

FIG. 2E is a plan view of the insulating layer 25 as seen from the top surface 11. The insulating layer 25 is the fifth insulating layer from the top surface 11 of the multilayer body 2. A surface of the insulating layer 25 on the side of the bottom surface 12, not on the side of the top surface 11, is provided with line conductors 42, 43, 44, 45, and 46 defining the wiring portion 5, and is also provided with the planar conductor 15 defining the shield electrode 4. The insulating layer 25 includes interlayer connection conductors 63, 64, 65, 67, 68, and 69 defining the wiring portion 5.

The interlayer connection conductor 63 passes through the insulating layer 25, and is connected to the interlayer connection conductor 60 in the fourth insulating layer 24 at an end portion thereof on the side of the top surface 11 and is also connected to the line conductor 42 at an end portion thereof on the side of the bottom surface 12. The line conductor 42 is connected to the filter output terminal of the surface mount device 8, with the interlayer connection conductors 63, 60, 57, 54, and 51, the pad conductors 39, 37, and 34, and the component connecting electrode 31 interposed therebetween. Then, on the surface of the insulating layer 25 on the side of the bottom surface 12, the line conductor 42 extends to a predetermined point near the outer edge in a corner portion corresponding to the surface mount device 8 mounted on the top surface 11.

The interlayer connection conductor 64 passes through the insulating layer 25, and is connected to the interlayer connection conductor 61 in the fourth insulating layer 24 at an end portion thereof on the side of the top surface 11 and is also connected to the line conductor 43 at an end portion thereof on the side of the bottom surface 12. The line conductor 43 is connected to the filter input terminal of the surface mount device 8, with the interlayer connection conductors 64, 61, 58, 56, and 53, the pad conductors 40 and 36, the line conductor 38, and the component connecting electrode 33 interposed therebetween. On the surface of the insulating layer 25 on the side of the bottom surface 12, the line conductor 43 extends from a corner portion corresponding to the surface mount device 8 mounted on the top surface 11 to a center portion overlapping the embedded component 3. The interlayer connection conductor 65 passes through the insulating layer 25, and is connected to the line conductor 43 at an end portion thereof on the side of the bottom surface 12 and is also connected to a terminal electrode (signal output terminal) (not shown) of the embedded component 3 at an end portion thereof on the side of the top surface 11.

The interlayer connection conductor 66 passes through the insulating layer 25, and is connected to the interlayer connection conductor 62 in the fourth insulating layer 24 at an end portion thereof on the side of the top surface 11 and is also connected to the line conductor 44 at an end portion thereof on the side of the bottom surface 12. The line conductor 44 is connected to the ground terminal of the surface mount device 8, with the interlayer connection conductors 66, 62, 59, 55, and 52, the pad conductor 41, the planar conductor 14, the line conductor 35, and the component connecting electrode 32 interposed therebetween. On the surface of the insulating layer 25 on the side of the bottom surface 12, the line conductor 44 extends from the vicinity of the outer edge to a center portion and is connected to the planar conductor 15. The interlayer connection conductor 67 passes through the insulating layer 25, and is connected to the line conductor 44 at an end portion thereof on the side of the bottom surface 12 and is also connected to a terminal electrode (ground terminal) (not shown) of the embedded component 3 at an end portion thereof on the side of the top surface 11.

The interlayer connection conductor 68 passes through the insulating layer 25, and is connected to the line conductor 45 at an end portion thereof on the side of the bottom surface 12 and is also connected to the terminal electrode (ground terminal) (not shown) of the embedded component 3 at an end portion thereof on the side of the top surface 11. On the surface of the insulating layer 25 on the side of the bottom surface 12, the line conductor 45 extends from the vicinity of the outer edge to the center portion and is connected to the planar conductor 15.

The interlayer connection conductor 69 passes through the insulating layer 25, and is connected to the line conductor 46 at an end portion thereof on the side of the bottom surface 12 and is also connected to a terminal electrode (supply voltage terminal) (not shown) of the embedded component 3 at an end portion thereof on the side of the top surface 11. On the surface of the insulating layer 25 on the side of the bottom surface 12, the line conductor 46 extends from the center portion to a predetermined point in the vicinity of the outer edge.

The planar conductor 15 defining the shield electrode 4 overlaps a portion of the bottom side of the embedded component 3. The planar conductor 15 is connected, via the line conductors 44 and 45, to the other planar conductor 14 defining the shield electrode 4, the ground terminal of the embedded component 3, and the ground terminal of the surface mount device 8.

Figure 2F:
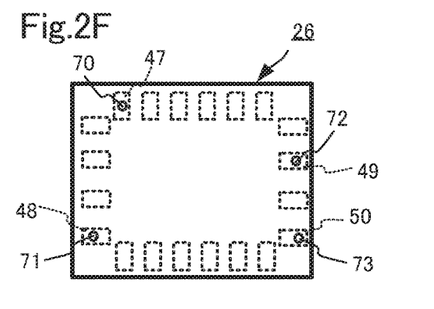

FIG. 2F is a plan view of the insulating layer 26 as seen from the top surface 11. The insulating layer 26 is the sixth insulating layer from the top surface 11 of the multilayer body 2, that is, an insulating layer exposed to the bottom surface 12. A surface of the insulating layer 26 on the side of the bottom surface 12, not on the side of the top surface 11, is provided with a plurality of pad conductors (including pad conductors 47, 48, 49, and 50) defining the external connecting portion 7. The insulating layer 26 includes interlayer connection conductors 70, 71, 72, and 73 defining the wiring portion 5.

The interlayer connection conductor 70 passes through the insulating layer 26, and is connected to the line conductor 42 on the fifth insulating layer 25 at an end portion thereof on the side of the top surface 11 and is also connected to the pad conductor 47 at an end portion thereof on the side of the bottom surface 12. The pad conductor 47 is thus connected to the filter output terminal of the surface mount device 8, with the interlayer connection conductors 70, 63, 60, 57, 54, and 51, the line conductor 42, the pad conductors 39, 37, and 34, and the component connecting electrode 31 interposed therebetween.

The interlayer connection conductor 71 passes through the insulating layer 26, and is connected to the line conductor 44 on the fifth insulating layer 25 at an end portion thereof on the side of the top surface 11 and is also connected to the pad conductor 48 at an end portion thereof on the side of the bottom surface 12. The pad conductor 48 is thus connected to the ground terminals of the surface mount device 8 and embedded component 3, with the interlayer connection conductors 71, 67, 66, 62, 59, 55, and 52, the line conductors 44 and 35, the planar conductor 14, the pad conductor 41, and the component connecting electrode 32 interposed therebetween.

The interlayer connection conductor 72 passes through the insulating layer 26, and is connected to the line conductor 45 on the fifth insulating layer 25 at an end portion thereof on the side of the top surface 11 and is also connected to the pad conductor 49 at an end portion thereof on the side of the bottom surface 12. The pad conductor 49 is thus connected to the ground terminals of the surface mount device 8 and embedded component 3, with the interlayer connection conductors 72, 68, 66, 62, 59, 55, and 52, the line conductors 45, 44, and 35, the planar conductor 14, the pad conductor 41, and the component connecting electrode 32 interposed therebetween.

The interlayer connection conductor 73 passes through the insulating layer 26, and is connected to the line conductor 46 on the fifth insulating layer 25 at an end portion thereof on the side of the top surface 11 and is also connected to the pad conductor 50 at an end portion thereof on the side of the bottom surface 12. The pad conductor 50 is thus connected to the supply voltage terminal of the embedded component 3, with the interlayer connection conductors 73 and 69 and the line conductor 46 interposed therebetween.

In the component-embedded substrate 1 configured as described above, the embedded component 3 is sandwiched in the stacking direction between two planar conductors 14 and 15 defining the shield electrode 4. The embedded component 3 is thus electromagnetically shielded from both sides in the stacking direction. Therefore, even when the embedded component 3 includes the oscillation circuit 13 which originates noise, electromagnetic noise generated by the oscillation circuit 13 is able to be prevented from negatively affecting the outside. At the same time, the embedded component 3 is able to be prevented from being negatively affected by electromagnetic noise from the outside. In the component-embedded substrate 1, the two planar conductors 14 and 15 each include a plurality of openings 16 dispersedly arranged. Therefore, even if cracks are formed in or around the embedded component 3 during manufacture of the component-embedded substrate 1, the internal structure of the component-embedded substrate 1 is able to be inspected by a substrate flaw detecting method using flaw detection waves, such as ultrasonic waves, X-rays, or infrared rays.

Figure 3:
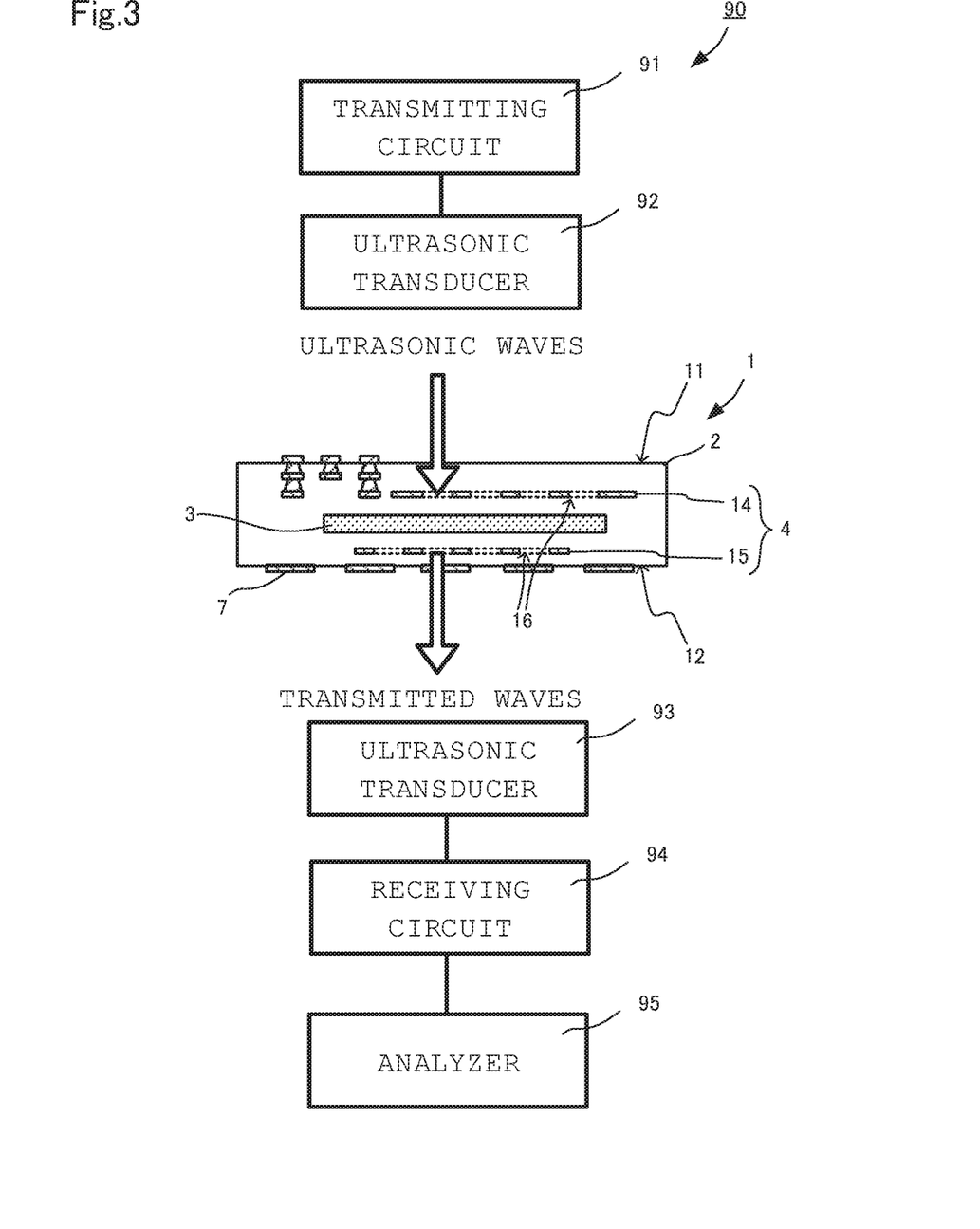
FIG. 3 is a schematic lateral view illustrating a first example of application of a substrate flaw detecting method to the component-embedded substrate according to a preferred embodiment of the present invention.

FIG. 3 schematically illustrates a first example of application of the substrate flaw detecting method to the component-embedded substrate 1. A substrate flaw detecting apparatus 90 includes a transmitting circuit 91, a transmitting ultrasonic transducer 92, a receiving ultrasonic transducer 93, a receiving circuit 94, and an analyzer 95. The transmitting circuit 91 outputs a drive voltage signal to the transmitting ultrasonic transducer 92. The transmitting ultrasonic transducer 92 includes a piezoelectric body. The ultrasonic transducer 92 vibrates in response to the drive voltage signal applied thereto, and transmits ultrasonic waves to space. The component-embedded substrate 1 is positioned, with the top surface 11 closely facing the transmitting ultrasonic transducer 92.

The ultrasonic waves transmitted from the transmitting ultrasonic transducer 92 hit the component-embedded substrate 1 in the thickness direction (stacking direction), thus causing ultrasonic vibration to be transmitted inside the component-embedded substrate 1 in the thickness direction. In the component-embedded substrate 1, this ultrasonic vibration is mainly transmitted through the multilayer body 2 (insulating layers), but significant reflection or absorption occurs in the shield electrode 4 having greater variation in density and elastic modulus than the multilayer body 2. As a result, when the embedded component 3 is covered by the shield electrode 4, the ultrasonic vibration reaching the embedded component 3 and its vicinity is normally significantly attenuated. However, in the component-embedded substrate 1, the planar conductor 14 defining the shield electrode 4 includes the openings 16 passing therethrough in the thickness direction. Therefore, the ultrasonic vibration is transmitted through the openings in the planar conductor 14 and reaches the embedded component 3 and its vicinity without significant attenuation. Thus, if cracks are formed in or around the embedded component 3, the cracks cause diffraction, dispersion, or absorption of the ultrasonic vibration. Ultrasonic waves passing through the embedded component 3 and its vicinity are also transmitted through the openings 16 in the planar conductor 15 on the other side of the embedded component 3 adjacent to the bottom surface 12, and pass through the bottom side of the component-embedded substrate 1 without significant attenuation.

In the substrate flaw detecting apparatus 90, the receiving ultrasonic transducer 93 is positioned to closely face the bottom side of the component-embedded substrate 1, and receives ultrasonic waves transmitted through the component-embedded substrate 1. In the component-embedded substrate 1, the shield electrode 4 includes the openings 16 and this prevents significant attenuation of ultrasonic waves. The receiving ultrasonic transducer 93 is thus able to receive the ultrasonic waves with intensity sufficient for detection of cracks.

The receiving ultrasonic transducer 93 converts the received ultrasonic vibration into an electrical signal. The receiving circuit 94 performs signal amplification and analog-to-digital conversion on the electrical signal detected by the receiving ultrasonic transducer 93. The analyzer 95 performs a predetermined computation on an output signal from the receiving circuit 94. In the component-embedded substrate 1, cracks have an impact on the intensity of ultrasonic vibration. The analyzer 95 analyzes a detection signal of ultrasonic vibration to generate a flow detection signal, such as image data representing the internal structure of the component-embedded substrate 1 or a signal representing the presence or absence of cracks, thus obtaining information of the internal structure of the component-embedded substrate 1 and non-destructively inspecting the internal structure of the component-embedded substrate 1. For example, when generating image data as a flow detection signal, the analyzer 95 detects changes in the intensity of reflected waves with time while varying the direction of transmission of ultrasonic waves. The analyzer 95 is thus able to generate image data which associates the intensity of reflected waves with the internal positional information of the component-embedded substrate 1.

Thus, by applying the substrate flaw detecting method using ultrasonic waves to the component-embedded substrate 1, it is possible to check for cracks formed in and around the embedded component 3 even when the embedded component 3 is electromagnetically shielded on both sides.

FIG. 3 illustrates the substrate flaw detecting method for inspecting the internal structure of the component-embedded substrate 1 using ultrasonic waves transmitted through the inside of the component-embedded substrate 1. Alternatively, ultrasonic waves reflected inside the component-embedded substrate 1 may be used to inspect the internal structure of the component-embedded substrate 1.

Figure 4:
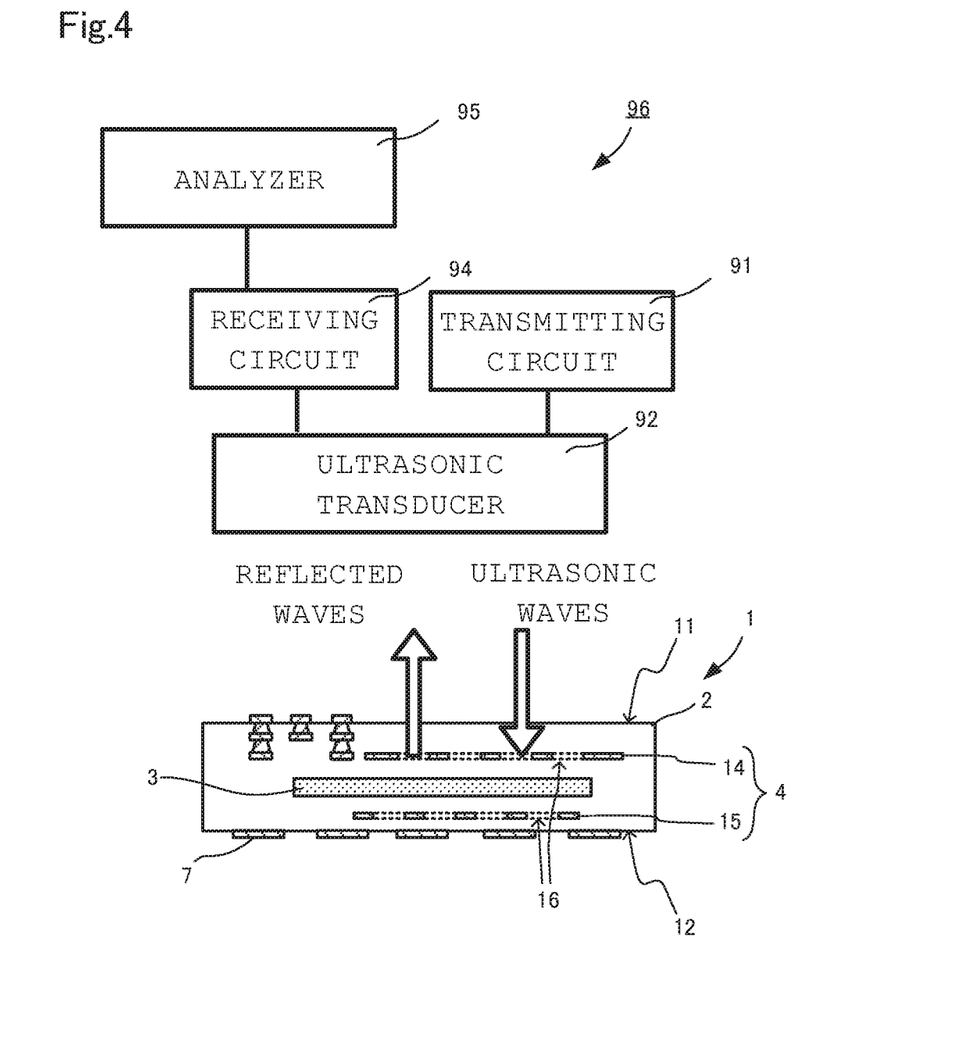
FIG. 4 is a schematic lateral view illustrating a second example of application of the substrate flaw detecting method to the component-embedded substrate according to a preferred embodiment of the present invention.

FIG. 4 schematically illustrates a second example of application of the substrate flaw detecting method to the component-embedded substrate 1. A substrate flaw detecting apparatus 96 has substantially the same configuration as the substrate flaw detecting apparatus 90 described above, except that the substrate flaw detecting apparatus 96 includes the ultrasonic transducer 92 alone. The transmitting circuit 91 and the receiving circuit 94 control the ultrasonic transducer 92 such that transmission of ultrasonic waves and reception of reflected waves are performed in a time-shared manner, and check for cracks formed in and around the embedded component 3 using reflected ultrasonic waves, instead of transmitted ultrasonic waves.

In the case of using reflected ultrasonic waves, it is preferable to alternately perform the step of transmitting ultrasonic waves from the side of the top surface 11 of the component-embedded substrate 1 and inspecting in detail the internal structure of the top side of the embedded component 3 using the received reflected waves, and the step of transmitting ultrasonic waves from the side of the bottom surface 12 of the component-embedded substrate 1 and inspecting in detail the internal structure of the bottom side of the embedded component 3 using the received reflected waves. This makes it possible to inspect in detail the internal structure of the internal regions of the component-embedded substrate 1 on the sides of both the top surface 11 and the bottom surface 12.

In the case of using reflected ultrasonic waves, the openings 16 of the two planar conductors 14 and 15 in the component-embedded substrate 1 do not necessarily need to coincide, that is, do not necessarily need to face each other in the stacking direction. The outer surface of the embedded component 3 may be shielded with a metal material. One of the two planar conductors 14 and 15 does not necessarily need to have the openings 16. Although a flaw detectable range in the component-embedded substrate 1 is narrowed in any of these cases, it is still possible to check for cracks in a region where ultrasonic waves are transmitted, at least in and around the embedded component 3.

Besides the substrate flaw detecting method using ultrasonic waves as described above, a substrate flaw detecting method using X-rays or infrared rays may be performed. X-rays and infrared rays are absorbed by planar conductors when transmitted through the component-embedded substrate 1. Accordingly, by providing a plurality of openings in the planar conductors, it is possible to allow X-rays or infrared rays to pass through the planar conductors, as in the case of using ultrasonic waves, thus checking for cracks in and around the embedded component.

X-rays and infrared rays are suitable for use when the embedded component is made of an element heavier than a light element, such as Si. In this case, using X-rays or infrared rays makes it possible to check for cracks in the embedded component with particularly high accuracy. On the other hand, ultrasonic waves are suitable for use when the embedded component is made of a light element, such as Si. In this case, using ultrasonic waves makes it possible to check for cracks in the embedded component with particularly high accuracy. In the case of using ultrasonic waves, since a difference in acoustic impedance between the planar conductors and the resin (insulating layers) causes reflection of the ultrasonic waves, the presence of the planar conductors has a greater impact than in the case of using X-rays or infrared rays. Accordingly, in the substrate flaw detecting method using ultrasonic waves, the benefit of forming a plurality of openings in the planar conductors is greater than that in the substrate flaw detecting method using X-rays or infrared rays.

Modifications of a planar conductor according to a preferred embodiment of the present invention will now be described.

Figure 5A:
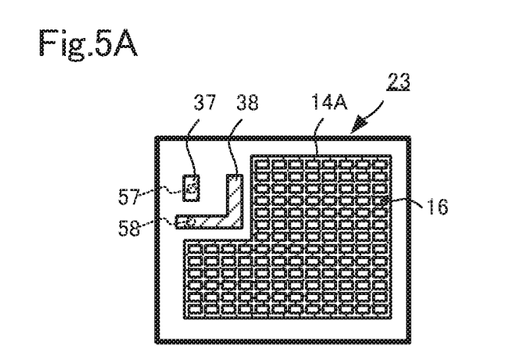
FIGS. 5A-5C are plan views each illustrating a modification of a shield electrode according to a preferred embodiment of the present invention.

FIG. 5A illustrates a planar conductor 14A according to a first modification according to a preferred embodiment of the present invention. The planar conductor 14A with a mesh shape is provided on the third insulating layer 23. The mesh shape includes a plurality of line conductor portions crossing each other. The embedded component 3 is electromagnetically shielded by the planar conductor 14A. Since the planar conductor 14A includes a plurality of openings 16 dispersedly arranged, ultrasonic waves used in a substrate flaw detecting method are able to pass through the planar conductor 14A.

Figure 5B:
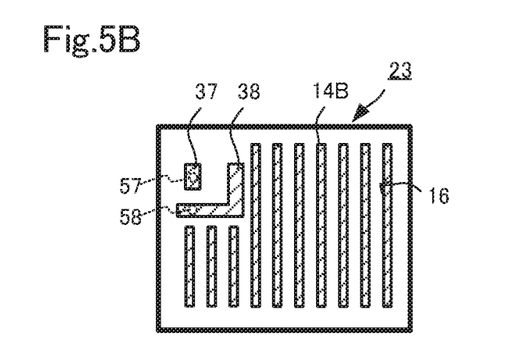

FIG. 5B illustrates a planar conductor 14B according to a second modification of a preferred embodiment of the present invention. The planar conductor 14B with a lattice shape is provided on the third insulating layer 23. The lattice shape includes a plurality of line conductor portions that parallel or substantially parallel to each other. Since the conductor portions of the planar conductor 14B are connected by respective interlayer connection conductors or the like to the ground potential, the embedded component 3 is electromagnetically shielded by the planar conductor 14B. Additionally, since a plurality of openings 16 corresponding to gaps between the conductor portions of the planar conductor 14B are dispersedly arranged, ultrasonic waves used in a substrate flaw detecting method are able to pass through the planar conductor 14B.

Figure 5C:
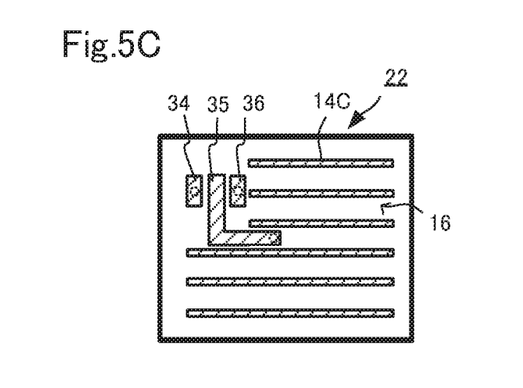

FIG. 5C illustrates a planar conductor 14C according to a third modification of a preferred embodiment of the present invention. The planar conductor 14C is provided with a lattice shape on the second insulating layer 22, not on the third insulating layer 23. The planar conductor 14C according to the third modification is preferably used in combination with the planar conductor 14B according to the second modification illustrated in FIG. 5B. That is, by overlaying the planar conductor 14B and the planar conductor 14C, the vertical lattice and the horizontal lattice on the different insulating layers 23 and 22 face each other to provide a mesh arrangement in perspective plan view. The embedded component 3 is thus electromagnetically shielded by the planar conductor 14B and the planar conductor 14C, and ultrasonic waves used in a substrate flaw detecting method are able to pass through the planar conductor 14B and the planar conductor 14C.

As described in each of the modifications of preferred embodiments of the present invention, a plurality of openings of appropriate shape are able to be provided in the planar conductor. The plurality of openings are preferably distributed over the entire surface of the planar conductor. This makes it possible to check for cracks with uniform accuracy throughout the periphery of the embedded component covered by the planar conductor.

Although the present invention can be carried out as described in the preferred embodiments, the component-embedded substrate of the present invention is not limited to the configuration of a surface mount type and may have other configurations. For example, the component-embedded substrate of the present invention may have a configuration in which an electronic component is embedded in a flexible cable substrate.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A component-embedded substrate comprising:
   a multilayer body including a plurality of insulating layers stacked in a stacking direction;
   an embedded component embedded in the multilayer body;
   a planar conductor disposed on one side of the embedded component in the stacking direction, the planar conductor overlapping the embedded component; and
   one or more wiring conductors disposed on the one side of the embedded component in the stacking direction, the one or more wiring conductors being different from the planar conductor and connecting to the embedded component or the planar conductor in the insulating layers; wherein
   the planar conductor includes a plurality of openings overlapping the embedded component over an entire region occupied by the embedded component, as seen in the stacking direction;
   the one or more wiring conductors are arranged to overlap the planar conductor and the embedded component; and
   at least one of the plurality of openings do not overlap at least a portion of any of the one or more wiring conductors different from the planar conductor, as seen in the stacking direction.

2. The component-embedded substrate according to claim 1, wherein the one or more wiring conductors include a line conductor extending around the openings and overlapping the embedded component and the planar conductor, as seen in the stacking direction.

3. The component-embedded substrate according to claim 1, wherein the planar conductor is connected to a ground potential.

4. The component-embedded substrate according to claim 3, wherein the embedded component includes an active element.

5. The component-embedded substrate according to claim 1, wherein the plurality of openings in the planar conductor are arranged at regular intervals.

6. The component-embedded substrate according to claim 5, wherein the planar conductor has a mesh shape or a lattice shape, as seen through the multilayer body in the stacking direction.

7. The component-embedded substrate according to claim 1, wherein
   a plurality of planar conductors are provided; and
   the plurality of planar conductors are disposed on both the one side and the other side of the embedded component in the stacking direction.

8. The component-embedded substrate according to claim 7, wherein the plurality of planar conductors sandwich the embedded component to define a shield electrode.

9. The component-embedded substrate according to claim 1, further comprising a shield electrode including the planar conductor, disposed inside the multilayer body and connected to a ground potential.

10. The component-embedded substrate according to claim 1, further comprising an oscillation circuit embedded in the embedded component at a location spaced from a position where the embedded component and a surface mount device overlap.

11. The component-embedded substrate according to claim 10, wherein the planar conductor overlaps an entirety of the oscillation circuit.

12. The component-embedded substrate according to claim 1, wherein the planar conductor overlaps an entire region occupied by the embedded component except for a region where the embedded component and a surface mount device overlap, as seen in the stacking direction.

13. The component-embedded substrate according to claim 1, further comprising interlayer connection conductors in the multilayer body to connect the one or more wiring conductors.

14. The component-embedded substrate according to claim 1, wherein the embedded component includes an oscillation circuit and is electromagnetically shielded from two sides.

15. A substrate flaw detecting method comprising:
    transmitting ultrasonic waves from one side of the component-embedded substrate according to claim 1 in the stacking direction;
    receiving the ultrasonic waves transmitted through the component-embedded substrate; and
    obtaining information of an internal structure of the component-embedded substrate based on an intensity of the ultrasonic waves received.

16. The method of claim 15, wherein the obtaining information includes analyzing a detection signal of ultrasonic vibration to generate a flaw detection signal.

17. The method of claim 15, wherein the obtaining information includes obtaining information including image data representing the internal structure of the component-embedded substrate.

18. The method of claim 15, wherein the obtaining information includes obtaining information regarding presence or absence of cracks in the internal structure of the component-embedded substrate.

19. The method of claim 15, wherein the method is performed using a substrate flaw detecting apparatus including a transmitting circuit, a transmitting ultrasonic transducer, a receiving ultrasonic transducer, a receiving circuit, and an analyzer.

20. The method of claim 15, wherein the method is performed using a substrate flaw detecting apparatus including an ultrasonic transducer.

* * * * *